Feb. 16, 1965 J. R. MITTLEIDER Plant Pat. 2,481
DIANTHUS PLANT
Filed Sept. 23, 1963
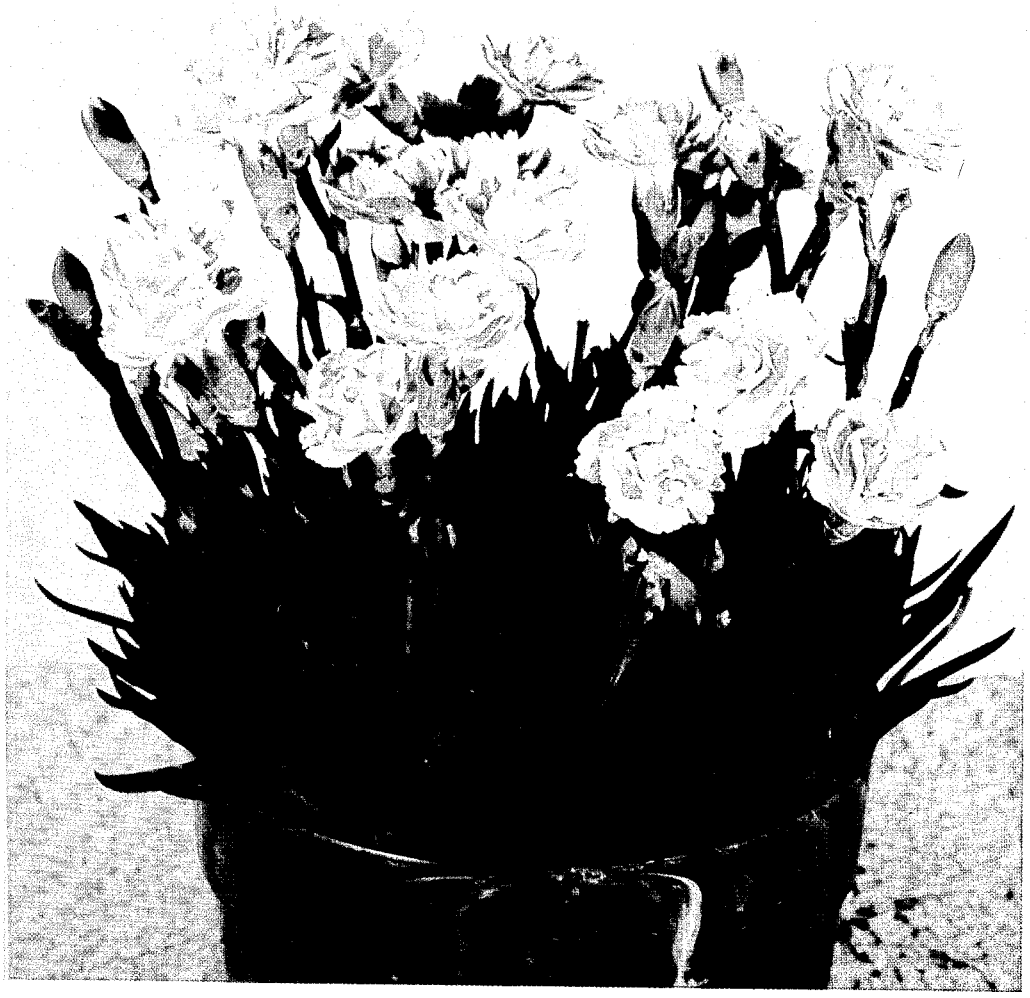
INVENTOR
JACOB R. MITTLEIDER
BY Herbert E. Kidder
AGENT United States Patent Office Plant Pat. 2,481
Patented Feb. 16, 1965

2,481
DIANTHUS PLANT

Jacob R. Mittleider, Loma Linda, Calif., assignor to Milo Academy, Inc., Milo, Oreg., a corporation of Oregon Filed Sept. 23, 1963, Ser. No. 310,965
1 Claim. (Cl. Pit.—71)

The present invention relates to a new and distinct variety of dianthus plant, which is characterized particularly by a low growing, compact, densely tufted plant bearing numerous small, double flowers of a soft, delicate rose color and, and having a very faint carnation-like fragrance.

The new and different plant variety is the result of an extensive breeding program at my nursery in Loma Linda, California, seeking new varieties of dianthus that would be especially suitable for mass plantings or edgings, without the necessity of staking the blooms. The characteristics sought were: (1) carnation foliage, (2) ever-blooming habit, (3) compactness, (4) fragrance, (5) full blooms, (6) strong stems, (7) hardiness and disease resistance, (8) pleasing new colors.

The present variety is the result of a three-step breeding program, in which Dianthus Rose Bowl (Plant Patent No. 2,034) was pollinated with pollen from Dianthus Old Spice (Plant Patent No. 499). Seedlings from this first cross, selected for foilage, were crossed with Dianthus Ruby Gem (unpatented), using pollen taken from this second cross to pollinate Ruby Gem. Seedlings from this second cross were "selfed," which is a term for artificially pollinating the plants of a group having the same genes. Out of several thousand seedlings resulting from this last step, I found one outstanding plant having the desired characteristics of very low-growing, compact, bushy plant form bearing many small, double flowers of a soft, delicate rose color, and having a very faint carnation-like fragrance.

The original reproduction of the plant by cuttings was carried out in the experimental section of my nursery at Loma Linda, California. Asexual reproduction of my new variety by cuttings, as performed by me at the nursery, shows that the characteristics and distinctions of the variety come true to form and are established and transmitted through succeeding propagations.

The plant grows best in well-drained, loamy soil, but is not critical as to the pH of the soil. Best blooms are obtained when the plant is grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Loma Linda, California, with color terminology and identifications in accordance with "A Dictionary of Color" by Maerz and Paul.

Plant:

*Form.*—Very low growing, compact and bushy, seldom exceeding two to three inches in height.

*Growing habit.*—Densely tufted.

*Blooming habit.*—Floriferous, flowering evenly over the entire plant, with blossoms ranging from ¾ of an inch to 1 inch in diameter, and ranging in number from 3 or 4 on one year old plants grown in three inch pots, up to 20 or more on two year old plants.

*Blooming season.*—Perpetual in southern California, or wherever the mean temperature is above 50° F. Where the mean temperature drops below 50° F., the plant becomes dormant and ceases to bloom. Maximum bloom in southern California occurs in the springtime, with heaviest bloom in April, May and June. Scattered blooming during most of the rest of the year except for August, and September, when blooming ceases and vegetative growth takes place.

*Foliage size.*—Maximum size of mature leaves on thrifty young plants is approximately 1½ to 2 inches in length, by three-sixteenths of an inch in width.

*Quantity.*—Abundant.

*Shape.*—Lanceolate, or grass-like.

*Color.*—Growing under good conditions, the color of mature leaves is a deep true green, almost exactly corresponding to Aspen Green (Plate 31–C–6 in Maerz and Paul's Color Dictionary).

*Texture.*—Glaucous.

Flower:

*Size.*—The maximum size is about 1 inch in diameter, with the average size being about ¾ inch across by about ⅜ inch high.

*Borne.*—At the end of the stem.

*Stem.*—Stiff and upright, approximately 4 to 5 inches long.

*Petalage.*—Double.

*Color.*—The flower is a uniform soft delicate rose color (Plate 2-H-2, Maerz and Paul).

*Petals.*—Firm in texture, of obovate form with regularly crenate margins. The size of the individual petals is about ½ inch to ¾ inch in length, by about ⅜ inch in width.

*Calyx.*—Spreading at the tip, with acuminate teeth, and approximately 1 inch in length.

Compared to other well-known dianthus plants, this new variety is distinguished by its very low-growing, compact form and large number of faintly fragrant, rather small double flowers of uniform delicate rose color, borne on stiff, upright stems that are four to five inches in length.

I claim:

A new and distinct variety of dianthus plant, substantially as shown and described herein, characterized particularly by its floriferous blooming habit, low-growing, compact, densely tufted plant form, usually not exceeding two to three inches in height, and bearing many small double flows of uniform soft delicate rose color, said flowers having a very faint carnation-like fragrance, and being borne on the ends of stiff, upright stems approximately 4 to 5 inches in height.

No references cited.